United States Patent [19]

Angstadt

[11] 4,104,311

[45] Aug. 1, 1978

[54] ORGANOMETALLIC COMPLEXES AS OXIDATION CATALYSTS

[75] Inventor: Howard P. Angstadt, Media, Pa.

[73] Assignee: Sun Ventures, Inc., St. Davids, Pa.

[21] Appl. No.: 525,548

[22] Filed: Nov. 20, 1974

Related U.S. Application Data

[63] Continuation-in-part of Ser. No. 801,187, Feb. 20, 1969, abandoned.

[51] Int. Cl.$^2$ .......................................... C07C 179/04
[52] U.S. Cl. ................................................. 260/610 B
[58] Field of Search ........................ 260/610 B, 610 A Primary Examiner—James O. Thomas, Jr.
Assistant Examiner—Werren B. Lone
Attorney, Agent, or Firm—J. Edward Hess; Donald R. Johnson; Stanford M. Back

[57] ABSTRACT

Organometallic complexes formed between trialkylphosphates and transition metal salts, including rare earth metals, have been found to be effective catalysts for the oxidation of olefins and secondary and tertiary alkylaromatics to form valuable oxidation products, particularly hydroperoxides, or their decomposition products.

13 Claims, No Drawings

ORGANOMETALLIC COMPLEXES AS OXIDATION CATALYSTS

CROSS-REFERENCE TO RELATED APPLICATIONS

This application is a continuation-in-part of U.S. Ser. No. 801,187 filed Feb. 20, 1969 now abandoned.

This application is related to the following application Ser. Nos. 772,421, Angstadt et al, 10-31-68; 777,493, Angstadt et al, 11-20-68; 773,633, Angstadt, 11-05-68; 787,582, Angstadt, 12-27-68; 853,547, Angstadt, 08-27-69.

The entire disclosure of all of the above six cases is hereby incorporated herein by reference.

BACKGROUND OF THE INVENTION

This invention relates to a novel process for the oxidation of olefins and secondary and tertiary alkylaromatic hydrocarbons to form various oxidation products, particularly hydroperoxides, or the decomposition products thereof, i.e. alcohols, aldehydes, ketones, and the like, or mixtures thereof. More particularly, this invention is directed to the use of complexes formed by reacting metal salts with a trialkylphosphate (TAP) as oxidation catalysts in the aforesaid process, and especially those complexes formed between TAP and lanthanide metal salts. The term "lanthanide metal salts" is intended to include the metal lanthanum as well as other metals in this series.

The oxidation of olefins and the alkyl side chains of aromatic compounds is already well known in the art. Thus, for example, it is known that tertiary alkylaromatics such as cumene can be auto-oxidized very slowly to form cumyl hydroperoxide when air or oxygen is rapidly passed through cumene warmed to about 80° C. Also, Canadian Patent No. 510,517 teaches that the rate of oxidation of cumene can be enhanced when carried out in the presence of alkali or alkaline earth metal oxides or hydroxides, or in the presence of salts and oxides of heavy metals. Under these conditions, the conversion rate is only 2 to 3 percent per hour. Other oxidation catalysts are likewise well known, but in most instances, again, the conversion rate is low, as is the overall yield of the desired oxidation product.

It is an object of this invention, therefore, to provide a novel process for the oxidation of olefins and secondary and tertiary alkylaromatic compounds whereby, in particular, the oxidation rate, or the selectivity, for hydroperoxide formation, or both, may be increased.

SUMMARY OF THE INVENTION

It has now been found, in accordance with the present invention, that organometallic complexes formed between metal salts, preferably those derived from transition metals (including metals of the lanthanide and actinide series), and trialkylphosphates are effective catalysts in the oxidation of olefins and secondary and tertiary alkylaromatic hydrocarbons. Certain of these catalysts, and particularly those derived from metal salts of the transition and lanthanide series, are especially effective in selectively forming the hydroperoxides to the substantial exclusion of hydroperoxide decomposition products.

DESCRIPTION OF THE PREFERRED EMBODIMENTS

The organometallic catalyst employed in the process of this invention, namely, the metal salt.TAP complexes, may be represented by the general formula

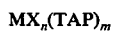

$$MX_n(TAP)_m$$

where M is a metal cation, preferably a transition metal from groups IIIB, IVB, VB, VIB, VIIB, VIIIB, IB, IIA or IIB of the periodic table, including the lanthanide and actinides; TAP is the aforementioned trialkylphosphate; X is the anion of the metal salt; $m$ is an integer of from 1 to 8; and $n$ is an integer of from 1 to 4. The alkyl moiety of the TAP may contain from 1 to 10 carbon atoms, preferably from 1 to 4 carbon atoms. Triethylphosphate (TMP) has been found to be especially useful in this invention, and although in the following description reference will be made to this particular compound, it will be understood to be merely representative of the TAP compounds generally.

These complexes may generally be prepared in one of two ways: (1) by direct fusion of a suitable metal salt with liquid TMP, or (2) by first dissolving the metal salt in, for example, 2,2-dimethoypropane followed by addition of TMP and evaporation of all liquids to provide the anhydrous metal salt.TMP complex.

Many of these TMP.metal complexes, and particularly those derived from lanthanide metals, preferentially give yields of hydroperoxides to the exclusion of hydrocarbon decomposition products at conversion rates of at least about 4 percent per hour. In the case of those remaining metal complexes which yield little or no detectable amounts of hydroperoxides in the final product, but which do yield other oxidation products, this is because the hydroperoxides which are first formed are then rapidly decomposed by the catalyst complex itself to form alcohols, aldehydes, ketones or the like. Thus, in the case of the olefins, for example, where oxidation is effected as shown by oxygen uptake yet no hydroperoxide, or only minor amounts, are found, there is recovered in the reaction mixture the corresponding alcohol and/or ketonic olefins and the like.

That is to say, since the known mechanism for the autoxidation of alkyl aromatic compounds includes the homolytic cleavage of the first formed intermediate, ie. the hydroperoxide, it is recognized that catalysts which accelerate this oxidation will also accelerate the decomposition of this intermediate. Hence it is possible to autoxidize the hydrocarbon to oxidized products without being able to detect the hydroperoxide intermediate because it is being decomposed to other oxidation products as rapidly as it is being formed. Therefore, the fact that no hydroperoxide is detected in the product does not mean it was not formed; it simply means that the catalyst is very effective in further converting this intermediate to aldehydes, ketones, alcohols; etc. In fact, the participation of hydroperoxides in the autoxidation of these hydrocarbons is so well established in the chemical literature that no other mechanistic pathways are seriously considered. See for example, G. A. Russell, J.A.C.S. 77, 4583–90, (1955); H. S. Blanchard, J.A.C.S. 82, 2014–21, (1959); J. A. Howard et al, *Canadian Jour. Chem.* 45 785–792 (1966); inter alia.

Thus, it will be evident to those skilled in the art that the exact nature of the oxidation product can readily be determind by routine experimentation with various catalyst but that in all cases it will be either an hydroperoxide and/or the decomposition products thereof as shown in the above-cited art, depending upon the exact catalyst composition chosen.

The metal salts used in forming the organometallic complexes are, as stated above, any metals of the periodic table, and preferably those derived from transition metals of groups IIIB, IVB, VB, VIB, VIIB, VIIIB, IB, IIA or IIB including the lanthanide and actinide metals.

The nature of the anion, X, is not critical, but may include any of the following inorganic or organic groups:

| | | | |
|---|---|---|---|
| $CN^-$ | cyanide | $AsO_3^=$ | arsenite |
| $NC^-$ | isocyanide | $AsO_4^{\equiv}$ | arsenate |
| $CN_2^=$ | cyanamide | $C_2H_3O_2^-$ | acetate* |
| $OCN^-$ | cyanate* | $C_4H_4O_6^=$ | tartrate |
| $CNO^-$ | isocyanate* | $C_7H_5O_2^-$ | benzoate |
| $ClO^-$ | chlorite | $B_4O_7^=$ | tetraborate |
| $ClO_2^-$ | chlorate | $BrO_3^-$ | bromate |
| $SCN^-$ | thiocyanate | $Cr_2O_7^=$ | dichromate |
| $CNS^-$ | isothiocyanate | $F^-$ | fluoride |
| $SeCN^-$ | selenocyanate | $CH_2O^-$ | formate |
| $S_2O_3^=$ | thiosulfate | $SeO_3^=$ | selenide |
| $SO_2^=$ | sulfite | $SeO_4^=$ | selenate |
| $SO_4^=$ | sulfate | $C_6H_5O^-$ | phenoxide |
| $S^=$ | sulfide | $C_2O_4^=$ | oxalate* |
| $HS^-$ | hydrosulfide | $O^=$ | oxide |
| $TeCN^-$ | tellurocyanate | $TeO_3^=$ | tellurite |
| $OCl^-$ | oxychloride | $AsS_3^{\equiv}$ | thioarsenite |
| $OH^-$ | hydroxide | $AsS_4^{\equiv}$ | thioarsenate |
| $NO_2^-$ | nitrite* | $Cl^-$ | chloride* |
| $PO_3^{\equiv}$ | phosphite | $Br^-$ | bromide* |
| $PO_4^{\equiv}$ | phosphate* | $NO_3^-$ | nitrate* |
| $CrO_4^=$ | chromate | $CO_3^=$ | carbonate* |
| $BO_3^{\equiv}$ | borate | $ClO_4^=$ | perchlorate* | in which those marked with an asterisk are most preferred.

As mentioned hereinabove, the oxidation products of the instant process are hydroperoxides, or the decomposition products thereof, i.e. alcohols, ketones, aldehydes, epoxides or mixtures thereof. Of these various products, maximization of the formation of the hydroperoxides is generally preferred inasmuch as those compounds derived from the alkylaromatic compounds are especially useful as intermediates in the preparation of such products as phenols, naphthols, acetone and the like, while those derived from the olefins are useful in facilitating the drying capabilities of polymers, i.e. they are useful as siccative agents.

The olefins employed as the starting materials in this process include any straight or branched chain unsaturated compounds having at least one hydrogen atom on the α-carbon atom, such as octene-1, and the like, as well as cyclic olefins having at least one hydrogen atom on the α-carbon atom, such as cyclohexene, cyclooctadiene, α-pinene, di-limonene and the like. These olefins may contain substituent groups which are non-reactive under the conditions of this process, as for example, ester, halo, nitro, alkyl or like groups which remain as substituents of the final product.

The secondary and tertiary alkylaromatic hydrocarbons employed as the starting materials in this process include compounds having the structural formula:

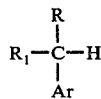

wherein R is lower alkyl; $R_1$ is lower alkyl or hydrogen; Ar is a substituted or unsubstituted aromatic nucleus such as phenyl or naphthyl; and wherein R and $R_1$ may be the same or different alkyl groups. The aromatic nucleus may be substituted by such groups as lower alkyl, lower alkoxy, halo, nitro or cyano radicals. Preferably, the secondary or tertiary alkylaromatic hydrocarbon is represented by such compounds as cumene, ethylbenzene, or sec.-butylnaphthalene, although it is understood that compounds such as n-butylbenzene, sec.-butylbenzene, isopropylnaphthalene and the like may also be employed. It will be understood that by "secondary" is meant those compounds of the formula

as defined above; while "tertiary" is intended to signify those compounds of the formula

as defined above, wherein $R_1$ is alkyl.

The process of this invention is conveniently carried out by the rapid passage of air or oxygen through a suitable reactor, to which has first been added a solution of the alkyl-aromatic starting material, although other solvents which are inert to the reaction of peroxidation may likewise be employed.

The air or oxygen should be brought into intimate contact with the liquid phase with vigorous agitation either mechanically by the use of high speed stirrers, or by aeration using suitable nozzles or the like.

Mechanical agitation has been found to be particularly effective in those cases where the rate at which the oxygenating gas is introduced into the reactor is low, i.e. below about 3 liters per hour. Thus, for example, when air is merely introduced at the surface of the reaction mixture, agitation by a commercially available reciprocating disc type stirrer (e.g. "Vibro-Mixer," Chemapec Company, Inc., Hoboken, New Jersey) has as four-fold over what is obtained with lesser amounts of agitation.

Alternatively, these increased rates may similarly be achieved, and mechanical agitation substantially or entirely dispensed with by appreciably increasing the rate at which air or oxygen is introduced into the reaction medium. This is preferably accomplished by bubbling the oxygenating gas through the reaction mixture, vigorously, desirably in such a manner as to insure maximum dispersal of the gas through the medium, as for example, by using fritted glass discs or the like. Depending upon the amount of liquid medium involved, the rate of oxygenating gas may generally vary from about 3 to 300 liters per hour.

The amount of catalyst employed will vary depending upon the nature and amount of material to be oxidized and the nature of the catalyst itself. In general, however, from about 0.01 to 5.0 parts by weight of catalyst per 100 parts of substrate, and preferably from 0.2 to 1.0 parts per 100 parts has been found to be satisfactory.

The rate of input of oxygen or air will likewise vary depending upon the reaction temperature and pressure employed. There should be provided an amount at least theoretically sufficient to convert the alkylaromatic compound to the corresponding hydroperoxide, and preferably an excess of this amount. In general, a flow rate ranging from 0.5 to 300 liters per hour is sufficient for most conversions, and preferably at least 3 liters per hour as described above. While the reaction is preferably carried out at atmospheric pressure, it is possible to employ an oxygen pressure of from about 0.2 atmospheres to 50 atmospheres, and preferably about 1 to 10 atmospheres. At these higher pressures the oxidation rate is found to increase substantially when the organometallic complexes are employed, and particularly those catalysts which are selective for hydroperoxide formation.

The reaction temperature may range from about 80° to 150° C, and preferably from 90° to 120° C. At temperatures above 150° C the catalysts tend to be thermally unstable.

The reaction is generally run for from half an hour to ten hours, depending upon the amount of substrate employed and the degree of conversion desired. When, however, a hydroperoxide is the principal product being formed, it is desirable that the reaction be terminated after a period of one to six hours at which point the reaction rate usually begins to taper off.

Advantageously, small amounts of a hydroperoxide, preferably one corresponding to the desired product, may be introduced into the reaction medium to act as a reaction initiator. Thus, for example, when cumene is being oxidized, it has been found to be advantageous to add small amounts of cumyl hydroperoxide in order to further accelerate the initial rate of reaction. The amount of hydroperoxide to be added is not critical, but 0.1 percent to 1.0 percent by weight of the starting material is preferred. It should be understood, however, that the addition of any such initiator will not change the nature of the product that would otherwise be obtained; the initiator serves only to reduce the induction time of the reaction.

The resulting products are readily recovered from the reaction medium by conventional methods. Thus, for example, a hydroperoxide may be conveniently recovered by isolating it as its sodium salt by addition of concentrated aqueous NaOH to the reaction product, followed by separation and drying of the hydroperoxide salt.

In the following examples, unless otherwise noted, both rate of conversion of the starting material and selectivity of the catalyst for converting the starting material to the corresponding hydroperoxide were measured. To measure rate of conversion, regardless of the nature of the oxidation product, the amount of oxygen uptake in a closed system was used; to measure the amount of hydroperoxide formed, samples of the reaction medium were periodically withdrawn and iodometrically titrated to determine the hydroperoxide content. On the basis of both of these figures the selectivity of any given catalyst for the formation of hydroperoxide could then be routinely determined.

EXAMPLE 1

Cumene Oxidation with Manganese Bromide . TMP Complex 12.0 g. of cumene (0.1 mole) was combined with 0.2 cc cumene hydroperoxide and 0.050 g. of $MnBr_2$. TMP (stoichiometry unknown), and heated to 100° C in an oxygen atmosphere with vigorous agitation such that good intermixing of the vapor and liquid phase was obtained. After 3 hours, 27.8 percent of the cumene had been converted, as measured by oxygen uptake, 25.6 percent of which was cumene hydroperoxide, as measured iodometrically. Under these conditions, in the absence of a catalyst, about 3 percent oxidation occurs.

EXAMPLE 2

Methyl Linoleate Oxidation with Lanthanum Chloride . TMP Complex

In accordance with the procedures of Example 1, 29.4 g. (0.10 mole) of methyl linoleate, 0.2 cc cumene hydroperoxide and 66.4 mg. of lanthanum chloride . TMP complex were heated together at 100° C. At the end of 50 minutes 19.3 percent of this unsaturated ester was converted quantitatively to a peroxidic product corresponding to the dihydroperoxide.

EXAMPLE 3

Cyclohexane Oxidation using Cobalt Chloride . TMP Complex

In accordance with the procedures of Example 1, 0.2 cc cumene hydroperoxide and 8 drops of $CoCl_2$. TMP in excess TMP gave, after one hour's oxidation at 67° C, a 23.6 percent conversion with 12.8 percent (54 percent selectivity) hydroperoxide. In the same time less than ½ percent of oxidation of cyclohexene occured in the absence of the catalyst.

EXAMPLE 4

Cyclohexene Oxidation using Manganese Bromide . TMP Complex

In accordance with the procedures of Example 1, when 50 mg. of manganese bromide . TMP complex is employed as the catalyst in oxidation of cyclohexene, there is obtained a 13 percent conversion in two hours with a quantitative production of cyclohexene hydroperoxide.

EXAMPLE 5

Decalin Oxidation using Manganese Bromide . TMP Complex

A large scale oxidation of cis-decalin using 158 g. of decalin, 1 ml. cumene hydroperoxide and 0.78 g. of manganese bromide . TMP complex gave, after 1 hour at 120° C, and 8.3 percent conversion of the hydrocarbon with 5.5 percent appearing as decalin hydroperoxide. Under these conditions in the absence of catalyst less than 2 percent occurs.

EXAMPLE 6

In accordance with the procedures of Example 1, but using lanthanum chloride trimethylphosphate complex as the catalyst, a 100% yield of hydroperoxide (7.7% conversion) is obtained after 2 hours. In the absence of any catalyst the conversion is 0.7%.

EXAMPLE 7

In accordance with the procedures of Example 1, but using cobalt chloride . tri(m-tolyl) phosphate as the catalyst, an oxidation rate of 15.1% is measured for the first hour with a 61% selectivity for cumene hydroperoxide. The remainder of the material is further oxidation products, i.e. cumyl alcohol, acetophenone, and traces of phenol.

EXAMPLE 8

In accordance with the procedures of Example 1, when 50 mg. of manganese bromide . tri-ethylphosphate complex is employed as the catalyst and tetralin is used as the substrate, there is obtained a 15% conversion in two hours with an essentially quantitative yield of tetralin hydroperoxide.

EXAMPLE 9

In accordance with the procedures of Example 1, when 50 mg. of ferrous nitrate . TMP complex is employed as the catalyst and tetralin is used as the substrate, there is obtained a rapid conversion of the tetralin into a mixture comprising tetralin hydroperoxide and its further oxidation products tetralol and tetralone.

EXAMPLE 10

In accordance with the procedures of Example 1, but using nickel acetate . TMP complex as the catalyst and ethylbenzene as the substrate, there is obtained in good yield a mixture of ethylbenzene hydroperoxide, acetophenone and methylphenyl carbinol.

The invention claimed is:

1. In the process for the catalytic oxidation of aliphatic or alicyclic olefins having at least one hydrogen atom on the α-carbon atom, said olefins having from 3 to 19 carbon atoms, or secondary or tertiary alkylaromatic hydrocarbons of the formula

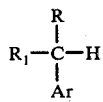

wherein R is lower alkyl; $R_1$ is lower alkyl or hydrogen; and Ar is an aromatic nucleus selected from the group consisting of phenyl and naphthyl, in the presence of air or oxygen at a temperature of from about 80° to 150° C to form hydroperoxides, the decomposition products thereof, or mixtures of the same, the improvement wherein the catalyst is of the formula

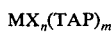

wherein TAP is a trialkylphosphate, the alkyl moiety of which has from one to four carbon atoms; MX is a metal salt wherein M is a transition metal cation of Group IB, IIB, IIIB, IVB, VB, VIB, VIIB, VIIIB or IIA of the Periodic Table and X is the anion of said metal salt; $m$ is an integer of from 1 to 8; and $n$ is an integer of from 1 to 4, wherein the ratio of said catalyst to said olefin or alkylaromatic hydrocarbon is from about 0.01 to 5.0 parts by weight of catalyst per 100 parts by weight of olefin or alkylaromatic hydrocarbon.

2. The process according to claim 1 wherein the trialkylphosphate is trimethylphosphate.

3. The process according to claim 1 wherein the reaction is carried out at a temperature of from 90° C to 120° C.

4. The process according to claim 1 wherein the alkylaromatic compound is cumene, the catalyst is trimethylphosphate and a lanthanide metal salt, and the product consists substantially of cumyl hydroperoxide.

5. The process according to claim 1 wherein the oxidation is carried out in the added presence of a hydroperoxide initiator.

6. The process according to claim 1 wherein the reaction is carried out under vigorous agitation.

7. The process according to claim 1 wherein the oxygen is introduced at a rate of from about 0.5 to 300 liters per hour.

8. The process according to claim 1 wherein the metal is of the lanthanide or actinide series.

9. The process according to claim 1 wherein the oxidation is carried out at an oxygen pressure of from 1 to 50 atmospheres.

10. The process according to claim 1 wherein the anion is a bromide, chloride, carbonate, nitrate or perchlorate.

11. The process according to claim 1 wherein the anion is a cyanide, cyanate, isocyanate, nitrite, phosphate, acetate or oxalate.

12. The process according to claim 1 wherein the hydroperoxide decomposition products are alcohols, aldehydes, ketones, or mixtures thereof.

13. The process according to claim 1 wherein the ratio of catalyst to substrate is in the range of from 0.5 to 1.0 parts by weight of catalyst per 100 parts of substrate.

* * * * *